United States Patent [19]

Sackmann et al.

[11] Patent Number: 4,568,421
[45] Date of Patent: Feb. 4, 1986

[54] MONOFLUOROTRIAZINYL COMPOUNDS, PROCESSES FOR THEIR PREPARATION AND THEIR USE AS SIZING AGENTS

[75] Inventors: Günter Sackmann; Horst Jäger, both of Leverkusen; Ulrich Beck, Bornheim; Heinz Bäumgen, Leverkusen, all of Fed. Rep. of Germany

[73] Assignee: Bayer Aktiengesellschaft, Leverkusen, Fed. Rep. of Germany

[21] Appl. No.: 537,476

[22] Filed: Sep. 30, 1983

[30] Foreign Application Priority Data

Oct. 23, 1982 [DE] Fed. Rep. of Germany ....... 3239366

[51] Int. Cl.[4] ............................. D21H 3/12
[52] U.S. Cl. ................................ 162/158; 162/179
[58] Field of Search ............... 162/158, 135, 136; 8/190; 544/194, 217; 427/395

[56] References Cited

U.S. PATENT DOCUMENTS 3,057,675 10/1962 Hiestand et al. .................. 8/190
3,214,325 10/1965 Gaertner ......................... 162/158

Primary Examiner—Peter Chin
Attorney, Agent, or Firm—Sprung, Horn, Kramer & Woods

[57] ABSTRACT

New monofluorotriazinyl compounds of the formula

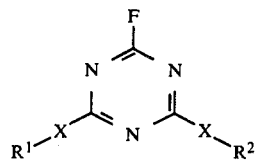

wherein
 $R^1$ and $R^2$ can be identical or different and represent a hydrocarbon radical with 12 to 24 C atoms and
 X represents an oxygen atom, a sulphur atom or the group $NR^3$,
wherein
 $R^3$ denotes hydrogen or a hydrocarbon radical with 1 to 24 C atoms.

In formula (1), the hydrocarbon radicals $R^1$ and $R^2$ preferably represent linear or branched alkyl ($C_{12}$–$C_{24}$), cycloalkyl ($C_{12}$–$C_{24}$) or aromatic radicals with fused-on hydroaromatic systems with 12 to 24 C atoms. The hydrocarbon radical $R^3$ is preferably one of the above-mentioned substituents or methyl.

The compounds of the formula (1) are suitable as effective components in reactive sizing agents for paper.

5 Claims, No Drawings

MONOFLUOROTRIAZINYL COMPOUNDS, PROCESSES FOR THEIR PREPARATION AND THEIR USE AS SIZING AGENTS

Sizing of paper on a paper machine is usually carried out with synthetic or natural sizing agents. Sizing can thereby occur by two different action mechanisms, depending on the type of sizing agent used. If non-reactive sizing agents, such as, for example, resin size, paraffin of certain synthetic high-molecular weight polymers, are used together with cationic fixing agents, such as, for example, aluminium sulphate or cationically charged polymers, sizing is effected by ionic fixing of the products onto the cellulose fibres. If reactive sizing agents are used, sizing is caused by the formation of covalent bonds between the sizing agent and the cellulose. Hydrophobic substances with functional groups which are capable of reacting chemically with the OH groups of cellulose are described as reactive sizing agents. Examples of reactive sizing agents which may be mentioned are: stearoyl-diketene, tetrapropenylsuccinic anhydride, stearyl isocyanate, dehydroabietyl isocyanate, epoxides and derivatives of cyanuric chloride.

Compared with the non-reactive sizing agents, the reactive sizing agents have the advantage that they are more effective since they are firmly bonded to the fibres. The amounts of sizing agent required to achieve a good sizing effect are thereby substantially lower than when non-reactive sizing agents are used.

Commercial products containing stearoyl-diketene as the active substance have chiefly gained acceptance on the market as reactive sizing agents.

These products have good to very good sizing properties when in the form of aqueous suspensions or solutions in organic solvents, especially on paper produced in a neutral or weakly alkaline medium. Paper produced in a neutral or weakly alkaline medium is usually understood as paper produced with $CaCO_3$ as the filler and without the addition of aluminium sulphate. However, a disadvantage of sizing agents based on stearoyl-diketene is that only a very slight sizing effect or none at all is achieved on paper which has been produced not with chalk but with kaolin as the filler.

It is therefore of interest to prepare sizing agents which are universally applicable, that is to say can be used both on neutral and on acid paper, and on paper containing chalk or kaolin as the filler.

The object of the invention was therefore to prepare a reactive sizing agent for paper which can be used on paper produced either in an acid or in a neutral to alkaline medium and of which the effectiveness is independent of the filler in the paper and of the presence of aluminium sulphate in the paper.

It has now been found that the new monofluorotriazinyl compounds of the formula

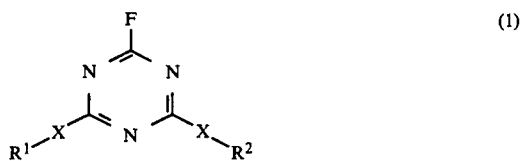

wherein
$R^1$ and $R^2$ can be identical or different and represent a hydrocarbon radical with 12 to 24 C atoms and
X represents an oxygen atom, a sulphur atom or the group $NR^3$,
wherein
$R^3$ denotes hydrogen or a hydrocarbon radical with 1 to 24 C atoms,
are particularly suitable as universally applicable active substances for sizing agents.

In formula (1), the hydrocarbon radicals $R^1$ and $R^2$ preferably represent linear or branched alkyl ($C_{12}$–$C_{24}$), cycloalkyl ($C_{12}$–$C_{24}$) or aromatic radicals with fused-on hydroaromatic systems with 12 to 24 C atoms. The hydrocarbon radical $R^3$ preferably represents one of the abovementioned substituents or methyl.

The invention preferably relates to compounds of the formulae (2), (3) and (4):

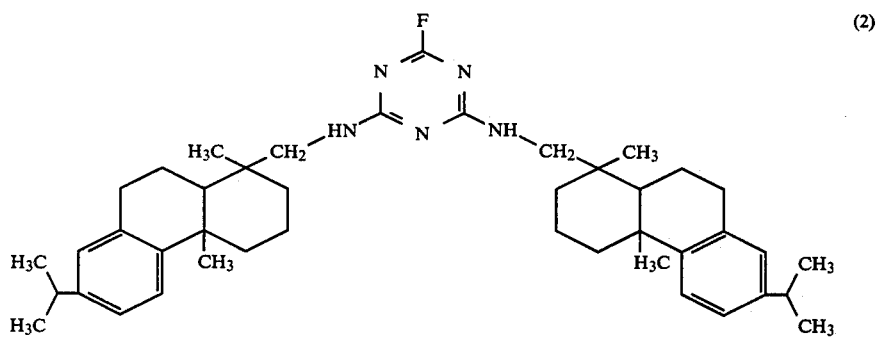

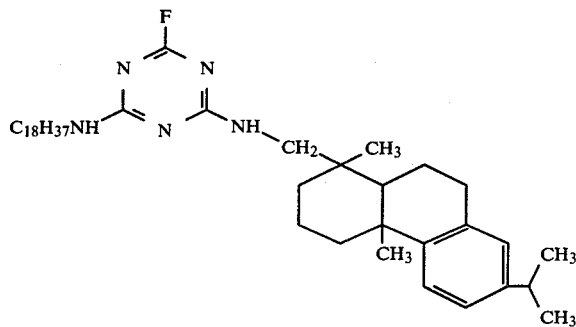
(4)

The invention furthermore relates to paper-sizing agents containing, as the active substance, a compound of the formulae (1), (2), (3) or (4).

Preferred sizing agents contain a cationic fixing agent as an additive.

The invention furthermore relates to a process for sizing paper, characterised in that compounds of the general formula (1)

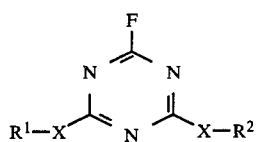
(1)

wherein $R^1$, $R^2$ and X have the abovementioned meaning, are used, either by themselves or in combination with cationic fixing agents, in paper-making.

The compounds of the formula (1) are prepared by a process in which trifluorotriazine (TFT) is reacted with monoamines, monoalcohols or mercaptans of the general formulae $R^1$—XH and/or $R^2$—XH wherein
$R^1$, $R^2$ and X have the abovementioned meaning.

Preferred suitable cationic fixing agents in combination with the monofluorotriazine derivatives of the formula (1) are aluminium salts (in particular aluminium sulphate) and cationically charged polymers. Polymers of this type are: copolymers or acrylamide and dimethylaminoethyl methacrylate, cationic polyamidoamines, polyamines containing urea groups, polyimines and cationic starch.

Examples of the monoamines and monoalcohols of the formulae $R^1$—XH and $R^2$—XH used are: dodecylamine, hexadecylamine, stearylamine, methyloctadecylamine, dodecanol, hexadecanol, stearyl alcohol and mixtures thereof.

However, in addition to linear or branched aliphatic monoamines or monoalcohols, it is also possible to use polynuclear, cycloaliphatic monoamines of monoalcohols. Examples of representatives of this group are abietylamine and dehydroabietylamine, as well as abietyl alcohol and dehydroabietyl alcohol.

The reactivity of the fluoride group of trifluorotriazines substituted by the above monoamines or monoalcohols towards cellulose is so great that, in contrast to cyanuric chloride, where two CL groups are necessary, just one fluorine substituent is sufficient to achieve good chemical fixing of the sizing agent to the paper fibre and hence an excellent sizing effect.

The following compounds (2), (3) and (4) are used as sizing agents in paper-making in a preferred embodiment of the invention:

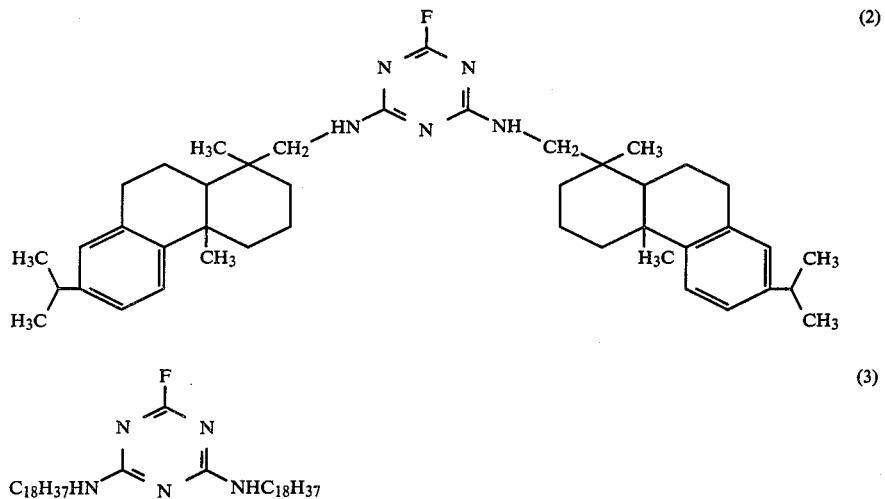

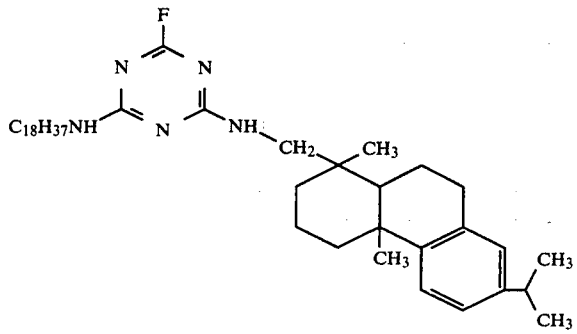

(4)

The paper-sizing process according to the invention can be either surface sizing or engine sizing. For this, the above hydrophobic monofluorotriazine derivatives of the formula (1) can be used in the form of solutions, for example in organic solvents, such as toluene or xylene, or in the form of aqueous formulations, for example in the form of suspensions or emulsions. Examples of particularly suitable suspending auxiliaries are polyvinyl alcohol and water-soluble cellulose derivatives, especially cationic starch, if necessary in combination with emulsifiers, which are preferably non-ionic. Weakly alkaline substances, such as $NaHCO_3$ or $Na_2CO_3$, can also be added to sizing agent preparations on an aqueous basis to accelerate the reaction between the compounds described and the cellulose fibres.

EXAMPLE 1

45 g of 92% strength dehydroabietylamine (0.145 mol) are dissolved in 500 ml of dried toluene. 14.8g (0.145 mol) of triethylamine are then added, and 9.75 g (0.072 mol) of trifluorotriazine are added dropwise at 0°-5°. The mixture is then warmed to 20°-25° C. and is stirred at this temperature for two hours. To remove the triethylamine hydrofluoride, the mixture is extracted by shaking with two 100 ml portions of water. 530 ml of a 9% strength solution of 2-fluoro-4,6-di-dehydroabietyl-aminotriazine in toluene are obtained.

EXAMPLE 2

Use of the product prepared according to Example 1 as a sizing agent: In order to determine the sizing properties of the trifluorotriazine derivative prepared according to Example 1 with as little interference as possible, that is to say in order to exclude all influences resulting from the formulation, the test described below is carried out with various types of paper. The types of paper used has the following compositions: (A) neutral: 50 parts of conifer wood sulphate, 50 parts of birch sulphate and 10 parts of chalk; (B) neutral: 50 parts of conifer wood sulphate, 50 parts of birch sulphate and 10 parts of kaolin; (C) acid: 50 parts of conifer wood sulphate, 50 parts of birch sulphate, 12 parts of kaolin and 1.5 parts of alaun.

The paper was finished with the sizing agent to be tested, as 0.1 or 0.2% strength solutions in toluene, on a padding unit and squeezed off. It was then subjected to the after-treatments I–IV below.

| Type of after-treatment | | Effect to be investigated |
|---|---|---|
| I | 5 minutes at 150° C. | Effect of the reacted sizing agent |
| II | 1 minute at 90° C. | Start of the reaction of the pure active compound at the temperatures of 120° C. customary in practice |
| III | 5 minutes at 90° C. between 2 wet filter papers | Influence of moisture |
| IV | Air-dried at 20° C. | Possible sizing without a chemical reaction |

The sized paper after-treated according to I–IV is cut into strips 3 cm wide and 9 cm long and placed on blue testing ink. After contact for 1 minute, the test paper is removed from the ink, the reverse side is squeezed off onto blotting paper and the paper is evaluated after 5 minutes. For qualitative evaluation of the penetration of the ink through the paper and hence the degree of sizing, the paper is rated with the numbers 1–5, individual numbers having the following meanings:

1: no penetration of ink
2: 5–10% penetration of ink
3: 10–20% penetration of ink
4: about 50% penetration of ink
4.5*: about 90% penetration of ink
5: 100% penetration of ink
*In addition, further intermediate values can also be used.

The table which follows shows the evaluation of the sizing effect of the sizing agent according to the invention on paper types A, B and C, according to the above scheme. For comparison with the prior art, the stearoyl-diketene used in many commercially available sizing agents was used as the active substance.

| | | Experimental results | | | | |
|---|---|---|---|---|---|---|
| | Solid in | Evaluation of sizing with after-treatment | | | | Average |
| Sizing agent | toluene | I | II | III | IV | evaluation |
| 1. Paper type A: (containing chalk, neutral) | | | | | | |
| Sizing agent according to the invention | 0.1% | 1 | 3 | 2.5 | 2.5 | 2.25 |
| Stearoyl diketene | 0.1% | 1 | 3.5 | 2.5 | 4.5 | 2.87 |
| 2. Paper type B: (containing kaolin, neutral) | | | | | | |
| Sizing agent according to the invention | 0.2% | 3 | 4.5 | 4 | 4.5 | 4.0 |
| Stearoyl diketene | 0.2% | 1.5 | 5 | 4.5 | 5 | 4.0 |
| 3. Paper type C: (containing kaolin, acid) | | | | | | |
| Sizing agent | 0.2% | 2 | 3 | 4 | 4 | 3.25 |

-continued

| Sizing agent | Solid in toluene | Evaluation of sizing with after-treatment | | | | Average evaluation |
|---|---|---|---|---|---|---|
| | | I | II | III | IV | |
| according to the invention Stearoyl diketene | 0.2% | 5 | 5 | 5 | 5 | 5 |

The experimental results listed clearly show that the sizing agent, according to the invention, based on disubstituted trifluorotriazine is superior to the stearoyl-diketene corresponding to the prior art on paper types A (containing chalk, neutral) and C (containing kaolin, acid), and gives an at least equivalent effect on paper type B (containing kaolin, neutral). The differences in the sizing effect of these two products particularly manifest themselves on paper type C. The paper used in this example contains kaolin as a filter and is produced in an acid medium with addition of aluminium sulphate, and is particularly relevant in practice since paper having this composition is frequently produced.

Whilst the paper treated with stearoyl-diketene shows complete penetration of the ink after the testing time with all four types of after-treatment, only substantially less penetration of the ink is to be observed within the same test period on the test pieces treated with the sizing agents according to the invention, this penetration being 5–10% (after-treatment I), 10–20% (after-treatment II) and about 50% (after-treatment III and IV).

We claim:

1. A paper containing as a sizing agent a monofluorotriazine compound of the formula

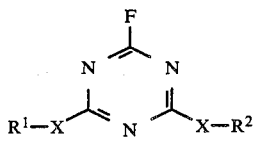

(1)

wherein $R^1$ and $R^2$ can be identical or different and represent a hydrocarbon radical with 12 to 24 C atoms and X represents an oxygen atom, a sulphur atom or the group $NR^3$, wherein $R^3$ denotes hydrogen or a hydrocarbon radical with 1 to 24 C atoms.

2. A paper of claim 1 wherein the monofluorotriazine sizing agent is one of the formula (1) according to claim 1, wherein $R^1$ and $R^2$ can be identical or different and represent linear or branched alkyl ($C_{12}$–$C_{24}$), cycloalkyl ($C_{12}$–$C_{24}$) or aromatic radicals with fused-on hydroaromatic systems with 12 to 24 C atoms, and wherein $R^3$ represents one of the abovementioned sustituents or methyl, and wherein X has the meaning given in claim 1.

3. A paper of claim 1 wherein the monofluorotriazine sizing agent is one of the formula

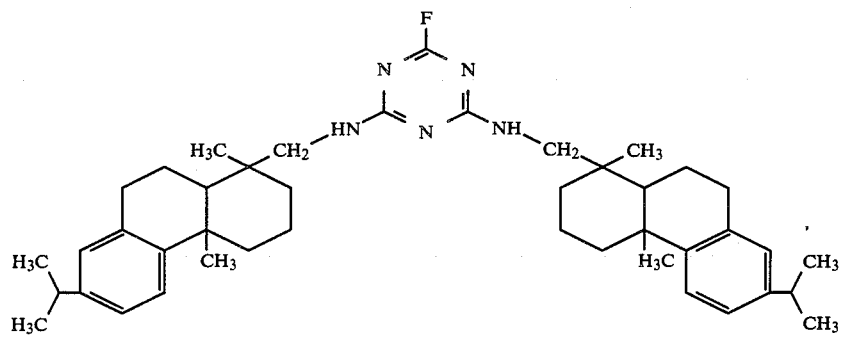

4. A paper of claim 1 wherein the monofluorotriazine sizing agent is one of the formula $$C_{18}H_{37}HN \quad N \quad NHC_{18}H_{37}$$

5. A paper of claim 1 wherein the monofluorotriazine sizing agent is one of the formula

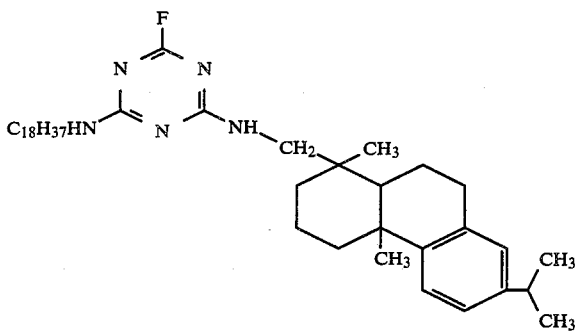

* * * * *